United States Patent
Hertzberg et al.

(10) Patent No.: US 10,695,220 B2
(45) Date of Patent: Jun. 30, 2020

(54) OPHTHALMOLOGICAL LASER TREATMENT SYSTEM

(71) Applicant: Ziemer Ophthalmic Systems AG, Port (CH)

(72) Inventors: Joachim Hertzberg, Thun (CH); Christian Rathjen, Bremen (DE)

(73) Assignee: Ziemer Ophthalmic Systems AG, Port (CH)

(*) Notice: Subject to any disclaimer, the term of this patent is extended or adjusted under 35 U.S.C. 154(b) by 33 days.

(21) Appl. No.: 14/835,067

(22) Filed: Aug. 25, 2015

(65) Prior Publication Data
US 2016/0051405 A1 Feb. 25, 2016

(30) Foreign Application Priority Data

Aug. 25, 2014 (EP) .................................. 14002939

(51) Int. Cl.
*A61F 9/008* (2006.01)

(52) U.S. Cl.
CPC .......... *A61F 9/008* (2013.01); *A61F 9/00804* (2013.01); *A61F 9/00825* (2013.01); *A61F 2009/00846* (2013.01); *A61F 2009/00897* (2013.01)

(58) Field of Classification Search
CPC .. A61F 9/008; A61F 9/00804; A61F 9/00825; A61F 2009/00846; A61F 2009/00897
USPC ............................................................ 606/4
See application file for complete search history.

(56) References Cited

U.S. PATENT DOCUMENTS

| | | | | |
|---|---|---|---|---|
| 2006/0106371 A1* | 5/2006 | Muhlhoff | ................ | A61F 9/008 606/5 |
| 2007/0010804 A1* | 1/2007 | Rathjen | .................... | A61F 9/008 606/5 |
| 2011/0102810 A1* | 5/2011 | Bischoff | ................. | A61F 9/008 356/614 |
| 2011/0118609 A1* | 5/2011 | Goldshleger | ....... | A61F 9/00834 600/476 |
| 2013/0158531 A1* | 6/2013 | Goldshleger | ....... | A61F 9/00825 606/6 |
| 2013/0338648 A1* | 12/2013 | Hanebuchi | .............. | A61F 9/008 606/4 |
| 2014/0104600 A1 | 4/2014 | Rathjen | | |
| 2016/0242848 A1* | 8/2016 | Moeskops | ............ | A61B 18/203 |

FOREIGN PATENT DOCUMENTS

WO 2004026198 A2 4/2004

* cited by examiner

*Primary Examiner* — Michael W Kahelin
*Assistant Examiner* — Vynn V Huh
(74) *Attorney, Agent, or Firm* — Banner & Witcoff, Ltd.

(57) ABSTRACT

An ophthalmological laser treatment system comprising a laser source (2) for producing laser radiation, a light projector (3) for focusing the laser radiation onto a focus (F) and a scanner system (5) for moving the focus (F) along a work line (p) comprises a monitoring system (6), which comprises a light detector (60) and is configured to monitor, by way of a light path (r), a monitored region (m) moving together with the focus (F). The monitoring system (6) is configured to monitor a monitored region (m), which moves together with the focus (F) with a fixed geometric assignment to the focus (F) and is for example disposed upstream of the focus (F) in the work direction and not yet worked on by laser radiation.

9 Claims, 2 Drawing Sheets

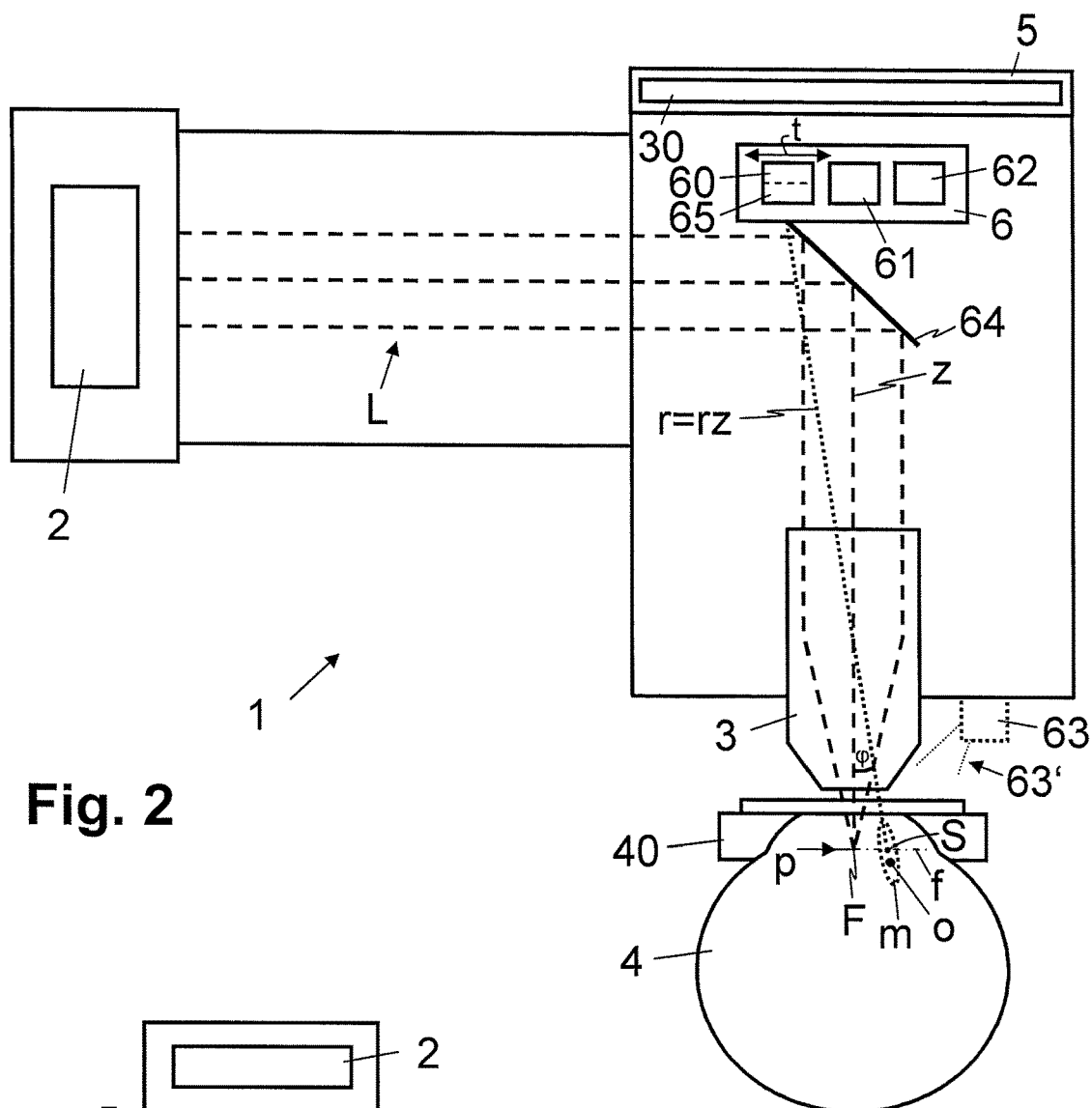
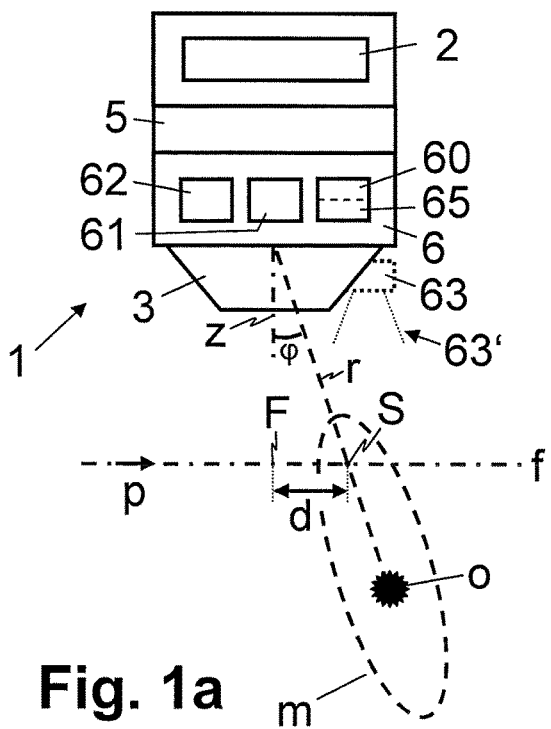
Fig. 1a
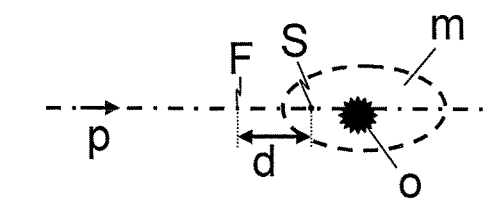
Fig. 1b

OPHTHALMOLOGICAL LASER TREATMENT SYSTEM

TECHNICAL FIELD

The present invention relates to an ophthalmological laser treatment system. The present invention relates in particular to an ophthalmological laser treatment system comprising a laser source for producing laser radiation, a light projector for focusing the laser radiation onto a focus and a scanner system for moving the focus along a work line.

PRIOR ART

In the treatment of eye tissue, for example for refractive correction of the cornea or lens, use is made of ophthalmological laser treatment systems which project laser radiation, in particular pulsed laser radiation, in focus along a work line in order thus to dissolve tissue or perform cuts in the tissue. In preparation, the geometry and topology of the eye to be treated and the structures thereof are registered and the planned work is defined by means of work data. However, since the actual treatment is performed on the living patient, it is not possible to preclude changes and positional changes of structures of the eye during the treatment. By way of example, intraocular structures may shift. By way of example, the iris or the posterior capsular bag may shift during the treatment. Moreover the movement of the whole eye cannot be completely excluded despite there being fixing patient cutting sites. Therefore, there is the risk of undesired positions in the eye being worked on or the focus being guided too close to such positions such that the wrong tissue regions or structures in the eye are worked on and/or strained too much by the pulsed laser beam, and so damage occurs via photochemical, photothermal and/or photoacoustic effects.

SUMMARY OF THE INVENTION

It is an object of the present invention to propose an ophthalmological laser treatment system which does not have at least some of the disadvantages of the prior art. In particular, it is an object of the present invention to propose an ophthalmological laser treatment system which renders it possible to identify positional changes of structures in the eye during the laser treatment of the eye.

In accordance with the present invention, these objects are achieved by the features of the independent claim. Moreover, further advantageous embodiments emerge from the dependent claims and the description.

The aforementioned objects are achieved by the present invention in particular by virtue of an ophthalmological laser treatment system, comprising a laser source for producing laser radiation, a light projector for focusing the laser radiation onto a focus and a scanner system for moving the focus along a work line, moreover comprising a monitoring system, which comprises a light detector and is configured to monitor, by way of a light path, a monitored region moving together with the focus. Monitoring a region moving together with the focus and with the scanning along the work line enables a targeted detection of positional changes of structures in the eye, or of the whole eye, relative to the laser treatment system during the laser treatment of the eye. As result, it is possible to detect eye structures or other objects, such as e.g. implants, which unexpectedly shift into the work region, i.e. onto the work line or into the vicinity of the focus or of the work line, before they are hit by the focussed laser radiation, in particular by a focussed laser pulse, or before they are too close in the surrounding region of the focussed laser radiation, in particular the surrounding region of a focussed laser pulse. Thus, it is possible to detect objects, such as eye structures or implants or the likes, before they are altered by the focussed laser radiation.

Compared to imaging and image processing methods and systems, in which generally the whole visible eye is registered by a camera in the top view and in which the registered top view image is processed with much outlay using an image processing processor and image processing algorithms, the present monitoring system is advantageous in that it is possible to dispense with complex processing electronics, processors and algorithms as a result of an optomechanical coupling and updating of the monitored region, as result of which higher processing speeds are obtainable with a lower system outlay. The detection of structures in the eye from the registered image data, required in imaging and image processing systems, is dispensed with by the optomechanical coupling and updating of the monitored region and by the monitoring by means of a comparatively simple light detector which, without requiring image processing, directly supplies detection signals for detecting structures or structure boundaries in the monitored region. Moreover, it is possible to preclude problems and erroneous behaviour in the active updating of imaging systems caused by software errors, hardware errors and calibration errors. Complicated method steps for verifying and validating image processing systems under very different operating modes and conditions also become unnecessary.

Depending on the embodiment, the monitoring system is configured to monitor, by way of the light path, a monitored region moving together with the focus in an optical or optomechanical manner. That is to say, the monitored region is optically or optomechanically coupled to the moving focus, as will be explained below.

In an embodiment, the monitoring system is configured to monitor, by way of the light path, a monitored region which moves together with the focus with a fixed geometric assignment to the focus. In the case of an unchanging focal depth, the fixed geometric assignment is e.g. defined by a fixed distance between the focus and the monitored region, e.g. a distance between the focus and a point of intersection of the light path with a focal surface placed through the focus.

Preferably, the light path is guided through the light projector to the light detector. In an embodiment, the light path is aligned along a detection axis, which has a defined alignment angle in relation to the optical axis z of the light projector. The alignment angle determines a further fixed geometric assignment of focus and monitored region if the laser radiation is not deflected from the optical axis of the light projector; here, the alignment angle remains unchanged, even in the case of different focal depths.

In a further embodiment, the alignment angle of the detection axis is adjustable in relation to the optical axis of the light projector. Therefore, it is possible to flexibly adjust the relative position of the monitored region in relation to the optical axis of the light projector.

In an embodiment, the scanner system comprises a drive device for moving the light projector along the work line and the light detector is fixedly connected to the light projector. In this embodiment, the monitored region is therefore coupled optomechanically to the moving focus and the monitored region moves optomechanically with the focus.

In an embodiment, the scanner system comprises at least one movable mirror for scanning the eye tissue with focussed laser radiation along the work line. The light detector is disposed upstream of the scanner system in relation to a beam path extending from the laser source to the light projector and the light path is guided to the light detector via the at least one mirror of the scanner system. Therefore, the monitored region in this embodiment is coupled optically to the moving focus and the monitored region moves optically with the focus. The relative position of the monitored region in relation to the optical axis of the light projector is determined e.g. by setting the alignment angle of the detection axis of the light detector in relation to the mirror of the scanner system.

In a further embodiment, the monitoring system is configured to perform depth monitoring in a monitored region extending in the direction of the light path.

In various embodiments, the monitoring system comprises an interferometric detection system, a detection system based on axial chromatic aberration with spectral evaluation, a confocal detection system and/or a triangulating detection system.

In an embodiment, the monitoring system comprises light-sensitive elements, which are configured to detect brightness values and/or spectral regions.

In an embodiment, the monitoring system comprises a light source for (active) illumination of the monitored region.

In an embodiment, the monitoring system is configured to monitor, by way of the light path, a monitored region, which moves together with the focus and is disposed upstream of the focus in the movement direction of the focus and is not yet worked on by the laser radiation.

In an embodiment, the monitoring system is configured to monitor a plurality of monitored regions moving together with the focus by way of a plurality of different light paths. The light paths intersect a focal surface placed through the focus at a different point of intersection with a fixed geometric assignment to the focus. Depending on the embodiment, the monitoring system comprises a plurality of light detectors, which are respectively assigned to a different light path, or a common light detector, to which the various light paths are fed for producing a composite signal.

In an embodiment, the laser treatment system comprises a data storage medium with geometry data of eye structures registered prior to the treatment and the monitoring system comprises a processing unit coupled to the light detector, which processing unit is configured to detect local deviations of the eye structures defined by the geometry data in the monitored region as a function of the geometry data and the detection signals of the light detector.

In an embodiment, the processing unit is configured to produce control signals for the laser treatment system when deviations are detected, wherein the control signals comprise a command for deactivating the laser source and/or for interrupting the projection of laser radiation.

In an embodiment, the monitoring system comprises a focusing system which is coupled into the light path and disposed upstream of the light detector. The focusing system is configured to adjust the depth position of the monitored region in the direction of the optical axis of the light projector.

In an embodiment, the monitoring system is configured to monitor, by way of the light path, the monitored region moving together with the focus, such as to detect objects before the objects are hit by focussed laser radiation.

In an embodiment, the monitoring system is configured to monitor, by way of the light path, the monitored region moving together with the focus, such as to detect objects before the objects are hit by a focussed laser pulse.

In an embodiment, the monitoring system is configured to monitor, by way of the light path, the monitored region moving together with the focus, such as to detect objects and to keep a defined safety distance between the focus and the objects.

In an embodiment, the monitoring system is configured to define the safety distance using a current value of power of the laser radiation.

BRIEF DESCRIPTION OF THE DRAWINGS

Below, an embodiment of the present invention is described on the basis of an example. The exemplary embodiment is illustrated by means of the following attached figures:

FIG. 1a schematically shows an ophthalmological laser treatment system comprising a monitoring system which, by means of a light detector, monitors a monitored region which is depicted in a cross section and moves together with the focus onto which the laser treatment system focuses laser radiation.

FIG. 1b schematically shows a monitored region in a top view, which monitored region moves with the focus along the work line with a fixed geometric assignment to the focus.

FIG. 2 schematically shows an ophthalmological laser treatment system comprising a light projector, which is moved by a drive device, for focusing the laser radiation and a co-moving light detector which monitors a monitored region moving with the focus.

WAYS OF IMPLEMENTING THE INVENTION

Figure 3:
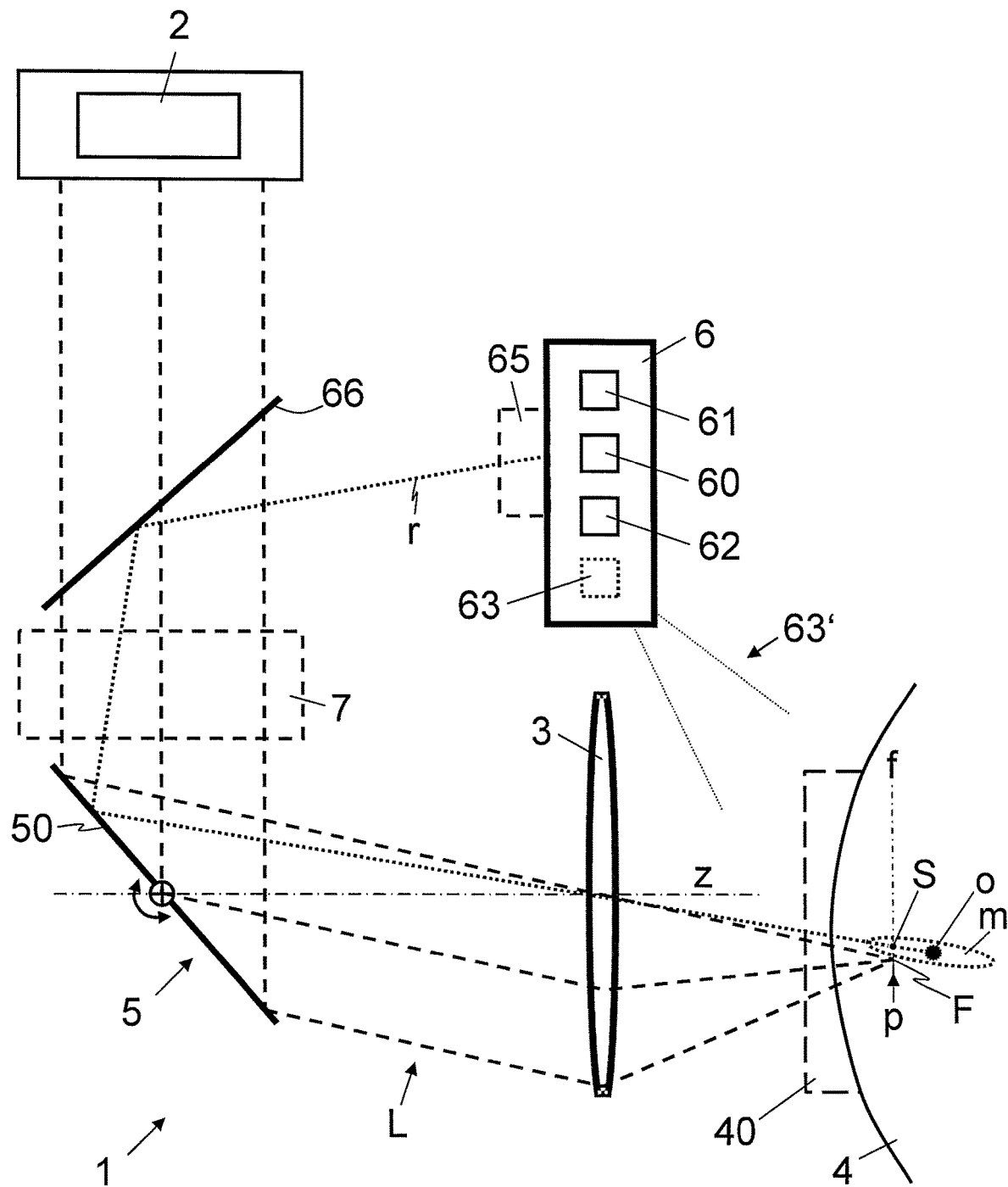
FIG. 3 schematically shows an ophthalmological laser treatment system comprising a movable mirror for scanning the eye tissue with focussed laser radiation and a monitoring system which, by way of a light path guided by the mirror, monitors a monitored region, depicted in a cross section, moving with the focus.

In FIGS. 1a, 2 and 3, reference sign 1 relates to an ophthalmological laser treatment system which comprises a laser source 2 for producing laser radiation L, a light projector 3 for focusing the laser radiation L onto a focus F and a scanner system 5 for moving the focus F along a work line p. In an embodiment, the laser source 2 is configured to produce pulsed laser radiation and for example comprises a femtolaser for generating femtolaser pulses L. A person skilled in the art will understand that, without departing from the subject matter of the claim, the laser sources 2 are usable for generating both pulsed and not pulsed laser radiation or laser beams. The ophthalmological laser treatment system generally comprises an optical transmission system (not depicted here), which is configured to transmit the pulsed laser beam from the laser source 2 to the light projector 3 in such a way that said laser beam enters the light projector 3 in a substantially collimated or at least approximately collimated manner. It should be noted here that the method or system presented here can also be converted or applied in a manner known to a person skilled in the art to non-collimated beam paths.

As depicted schematically in FIGS. 2 and 3, the ophthalmological laser treatment system 1 optionally comprises a patient interface 40, for example a suction ring with or without contact bodies, by means of which the eye of the patient is fixed during the treatment.

In the embodiment of FIG. 2, the scanner system 5 comprises a drive device 30, for example an electric motor, which is coupled to the light projector 3 for moving the light projector 3 along a work line p. As a result of the movement of the light projector 3, the focus F, onto which the laser radiation L (or the laser pulses) is/are focussed by the light projector 3, is also moved therewith.

In the embodiment of FIG. 3, the scanner system 5 comprises one or more movable mirrors 50, which are e.g. rotatable about one or more mirror axes, for scanning the eye tissue 4 with focussed laser radiation (or with focussed laser pulses) along a work line p. The laser radiation L (or the pulsed laser beam) is deflected by the mirror/mirrors 50 in such a way that the focus F, onto which said laser radiation (or pulsed laser beam) is focussed by the light projector 3, is moved along the work line p.

In both embodiments the laser treatment system 1 moreover comprises a monitoring system 6 which is configured to monitor a monitored region m which moves with the focus F with a fixed geometric assignment to the focus F. The monitoring system 6 comprises a light detector 60, a processing unit 61 and a data storage medium 62. Optionally, the monitoring system 6 moreover comprises a light source 63, e.g. one or more LEDs, for illuminating the monitored region m. In addition to an external illumination, it is also possible to illuminate along the light path r. The light detector 60 comprises light-sensitive elements, e.g. photodiodes or other light sensors, which are configured to detect brightness values and/or spectral regions. Brightness sensitive photodiodes are used to detect structure transitions or boundaries, for example from the black pupil to the bright iris. Spectrally sensitive photodiodes are used to detect specific structures with a predetermined colour spectrum, for example a defined colour spectrum region for detecting the iris. The monitoring system 6 is configured to supply light from the monitored region m to the light detector 60 by means of a light path r, which light is reflected by the eye tissue 4 and other objects o in the monitored region m as a result of ambient light, irradiated laser radiation L and/or illumination light 63' of the light source 63.

The processing unit 61 is connected to the light detector 60 by way of the signal lines and configured to receive and evaluate detection signals from the light detector 60. The processing unit 61 is connected by way of data lines to the data storage medium 62 and configured to read and evaluate geometry data of eye structures in the data storage medium 62. In one variant, the processing unit 61 is moreover configured to store the geometry data of eye structures in the data storage medium 62, which geometry data is registered prior to the treatment and, for example, supplied from an internal or external measurement system via a data line. The geometry data comprise topology, form, outline, size, position and/or arrangement of eye structures such as the cornea, iris, pupil, sclera, limbus, lens, retina and/or vitreous humour, and also other objects o such as implants or other foreign bodies in the eye tissue 4. The processing unit 61 is configured to detect, depending on the geometry data and detection signals of the light detector 60, whether the detection signals from the monitored region m, supplied by the light detector 60, indicate spatial deviations of the structures in the eye defined by the geometry data. Here, the processing unit 61 only considers detection signals of monitored regions m which were not yet worked on in order to avoid false detections based on changes in the eye tissue 4 caused by the laser work. The processing unit 61 is configured to produce control signals for the laser treatment system 1 if deviations are detected, which control signals deactivate the laser source 2 and/or interrupt the projection of laser radiation L (or of laser pulses) if the deviations indicate an unexpected position of structures along the work line p. The processing unit 61 comprises a circuit, for example one or more processors or other programmable logic units which are configured to compare the structures in the monitored region m defined by the stored geometry data in respect of the position thereof to the structures or structure boundaries detected by the light detector 60 in order to detect unwanted positional changes of the structures during the treatment and in order to abort or at least interrupt the treatment.

Thus, the processing unit 61 in connection with the light detector 60 makes it possible to detect objects, particularly objects defined by the geometry data, before they are altered by the focussed laser radiation. In an embodiment, a power or energy threshold, e.g. a defined threshold value of $W/cm^2$ or $J/cm^2$, respectively, is used to determine a safety distance between the focus F of the focussed laser beam or laser pulse. The safety distance is determined by taking into consideration the actual energy or power of the laser beam. Using the safety distance, the processing unit 61 aborts or at least interrupts the treatment, if the distance between the focus F and the detected object is smaller than the safety distance. Accordingly, the processing unit 61 is configured to ensure that a safety distance is kept between the focus F and objects detected by the light detector 60.

At this point, reference should clearly be made to the fact that, in contrast to the imaging or image processing methods or systems, the detection signals supplied by the light detector 60 do not require image processing but are compared directly to the location-specific structure information m which is gathered by the processing unit 61 from the geometry data for the monitored region m. Depending on the embodiment of the light detector 60, brightness values and/or colour values (spectral values) supplied by the detection signals are compared in a location-specific manner to corresponding values from the geometry data.

In the embodiment in FIG. 2, the light detector 60 is securely connected to the light projector 3 and also moved along the work line p when the light projector 3 is moved. The light detector 60 is configured to monitor the monitored region m by way of a light path r extending through the light projector 3. The light path r is aligned along a detection axis rz, which has a defined alignment angle φ in relation to the optical axis z of the light projector 3. As a result of the light detector 60 being moved together with the light projector 3, the alignment angle φ of the detection axis rz of the light detector 60 in relation to the optical axis z of the light projector 3 defines a fixed geometric assignment of the monitored region m to the focus F of the light projector 3, which assignment is maintained even if the light projector 3, or the focus F thereof, is moved. In the special case where the alignment angle φ is zero, the monitored region m is concentric with the focus F of the light projector 3 (and surrounds the focus F with a larger radius than the spot size of a focussed laser beam or laser pulse). Otherwise, the light path r extends along a detection axis rz angled to the optical axis z of the light projector 3 at an alignment angle φ, as is depicted in FIGS. 1a and 2. In the case of an unchanging depth of the focus F in the direction of the optical axis z of the light projector 3, the geometric assignment in respect of the distance d of the monitored region m from the focus F also remains constant here, wherein the distance d is depicted in FIGS. 1a, (cross section) and 1b (top view) as the distance of the focus F from the point of intersection S of the light path r with a focal surface f of the light projector 3.

FIGS. 1a, 1b, 2 and 3 illustrate a monitored region m disposed upstream of the focus F in the work direction (indicated by an arrow on the work line p), which monitored region, in a forward-looking manner, covers a region of the eye tissue 4, which has not yet been worked on and lies in front of the currently worked-on tissue.

As illustrated in FIG. 2, the pulsed laser beam is guided from the laser source 2 to the movable light projector 3 by a deflection mirror 64. The light path r or the detection axis rz leads through an opening (or a spectrally selective coating or a small introduced mirror) in the deflection mirror 64, or past the deflection mirror 64, to the light detector 60. In an embodiment, the alignment angle φ of the detection axis rz in relation to the optical axis z of the light projector 3 is adjustable. To this end, the position of the light detector 60 relative to the light projector 3 is modifiable, for example by displacing the light detector 60 along a translation axis t, which is normal to the projection axis z and aligned in the direction of the work line p. In a further embodiment, the extent of the monitored region m is adjustable, for example by way of an adjustable pinhole aperture, which restricts the light fed to the light detector 60.

In the embodiment of FIG. 3, the light path r leads through the light projector 3 and via the one or more mirrors 50 of the scanner system 5 to the light detector 60. That is to say, the light detector 60 is disposed upstream of the scanner system 5 in the beam path from the laser source 2 to the light projector 3 (or disposed downstream of the scanner system 5 in the beam path from the light projector 3 to the laser source). The light detector 60 is coupled by an optical element 66, e.g. a semitransparent mirror or a beam splitter, onto the light path r to the monitored region m. By disposing the light detector 60 upstream of the scanner system 5 and guiding the light path r over the mirror/mirrors 50 of the scanner system 5, the monitored region m is also moved with a fixed geometric assignment to the focus in the case of the deflection of the laser radiation (or laser pulses) caused by the movement of the mirror/mirrors 50 and the movement of the focus F of the focussed laser radiation (or of the pulsed laser beam) along the work line p obtained thereby. In other words, the light path r is scanned synchronously with the pulsed laser beam along the work line p as a result of the scanning movement of the mirror/mirrors 50 of the scanner system, and so the monitored region m is guided together with the movement of the focus F of the projected laser radiation (or laser pulses) along the work line p.

In one variant of the ophthalmological laser treatment system 1, in which a divergence modulator 7 is arranged in the beam path from the laser source 2 to the light projector 3, the light detector 60 is disposed upstream of the divergence modulator 7 such that focus changes in the projected laser radiation (or laser pulses) caused by a divergence modulation are accordingly also undertaken in the light path r and therefore also undertaken for the monitored region m. This correspondingly also applies to focal changes by the light projector 3, and so the geometric assignment of the monitored region m to the focus F is maintained, even in the case of focal displacements in the projection direction, and the monitored region m is also moved together with the focus F in the projection direction with a fixed geometric assignment to the focus F. In applications in which a co-movement of the monitored region m in the projection direction is undesired in variants with divergence modulators 7, the light detector 60 is disposed downstream of the divergence modulator 7.

In an embodiment, the depth position of the monitored region m is adjustable in the direction of the optical axis z of the light projector 3. To this end, the monitoring system 6 comprises a focusing system 65 disposed upstream of the light detector 60 in the light path r, which focusing system has one or more displaceable lenses.

In an embodiment, the monitoring system 6 is configured to carry out depth monitoring in a monitored region m extending in the projection direction or in the direction of the light path r, in particular in a monitored region m which also comprises a region lying below the focal surface f in the projection direction, as is schematically depicted in FIGS. 1a, 2 and 3. To this end, the monitoring system 6 comprises an interferometric detection system, a detection system based on chromatic aberration, a confocal detection system and/or a triangulating detection system. Depending on the embodiment, the monitoring system 6 has a depth-resolving detection system in addition to a detection system without depth resolution, for example light detectors 60 with the aforementioned photodiodes.

It should be noted here that the monitoring system 6 is configured to monitor, by way of the light path r, a monitored region m moving together with the focus F, which comprises not only movements of the focus F in the movement direction on the work line p in the x/y-direction normal to the optical axis z of the light projector 3, but also in the z projection direction. For the purposes of positioning a monitored region m moving together with the focus F in the z- or projection direction, provision is made In an embodiment for an additional focusing module, which is inserted into the light path r, which is disposed upstream of the light projector 3 and which renders adjustable the geometric assignment of the monitored region m in relation to the focus F for focus shifts in the projection direction.

It should moreover be noted here that, in further embodiments, the monitoring system 6 comprises a plurality of light detectors 60 or detection systems for monitoring a plurality of monitored regions m moving together with the focus F. Here, these light detectors 60 or detection systems are configured to monitor the various monitored regions m by way of a plurality of different light paths r, which each intersect a focal surface f placed through the focus F at a different point of intersection S with a fixed geometric assignment to the focus F. In an embodiment, the various light paths r are configured in such a way in said case that a plurality of monitored regions m are monitored, for example by means of diffractive optics, the light paths of which monitored regions are then all guided to a common light detector 60, where a composite signal is produced therefrom. A plurality of optical waveguides are provided in a further variant. The various monitored regions m are arranged in a region surrounding the focus F. A high detection rate with low latency times is achieved by monitoring a plurality of restricted regions, selected in a targeted manner, in the vicinity of the focus F, which is more efficient than what is possible using e.g. imaging systems.

The invention claimed is:
1. A laser treatment system comprising:
a laser source configured to produce laser radiation;
a light projector configured to focus the laser radiation onto a focus;
a scanner system comprising a mirror disposed upstream of the light projector in a laser beam path from the laser source to the light projector, the mirror being configured to perform scanning movements to scan eye tissue with focused laser radiation by movement of the focus along a work line in a movement direction normal to an optical axis of the light projector; and a monitoring system comprising a light detector disposed downstream of the laser source and upstream of the scanner system, the light detector being coupled by an optical element onto a light path which is guided over the mirror of the scanner system and lead through the light projector to receive, via the light path, light reflected in a monitored region of an eye, which the monitored region is moved along the work line by the scanning movements of the mirror of the scanner system synchronously with the movement of the focus, wherein the light detector has a detection axis set with a non-zero alignment angle in relation to the laser beam path to determine with a fixed geometric assignment a relative position of the monitored region in relation to the focus, such that the monitored region is disposed in the movement direction of the focus, ahead of the focus, and not yet worked on by the laser radiation.

2. The laser treatment system of claim 1, wherein the monitoring system comprises a processing unit configured to perform depth monitoring in the monitored region extending in the direction of the light path, wherein the depth monitoring is performed based on one or more of interferometric detection, chromatic aberration, confocal detection, or triangulation detection.

3. The laser treatment system of claim 1, wherein the monitoring system comprises at least one of: an interferometric detection system, a detection system based on axial chromatic aberration with spectral evaluation, a confocal detection system, and a triangulating detection system.

4. The laser treatment system of claim 1, wherein the light detector comprises light-sensitive elements configured to detect at least one of brightness values and spectral regions.

5. The laser treatment system of claim 1, wherein the monitoring system comprises a light source for illumination of the monitored region.

6. The laser treatment system of claim 1, wherein the laser treatment system comprises a data storage medium with geometry data of eye structures registered prior to treatment, and, the monitoring system comprises a processing unit coupled to the light detector, the processing unit configured to detect local deviations of the eye structures defined by the geometry data in the monitored region as a function of the geometry data and the detection signals of the light detector.

7. The laser treatment system of claim 6, wherein the processing unit is configured to produce control signals for the laser treatment system when deviations are detected, the control signals comprising at least one command from the following: deactivating the laser source and interrupting projection of the laser radiation.

8. The laser treatment system of claim 1, wherein the monitoring system comprises a focusing system which is coupled into the light path and disposed upstream of the light detector.

9. The laser treatment system of claim 1, wherein the monitoring system comprises a processing unit configured to determine a safety distance using a current value of power of the laser radiation, to detect objects in the monitored region, and to interrupt treatment, if a distance between the focus and a detected object is smaller than the safety distance.

* * * * *